United States Patent [19]

Sangha et al.

[11] Patent Number: 5,204,267
[45] Date of Patent: Apr. 20, 1993

[54] METHOD OF GLUCOSE STABILIZATION AND ANALYSIS IN DRIED BLOOD SPOT SAMPLES

[75] Inventors: Jangbir S. Sangha, Overland Park; Linda R. Pflatzgraff, Osawatomie; Melinda L. Van Hercke, Olathe, all of Kans.

[73] Assignee: Osborn Laboratories, Inc., Olathe, Kans.

[21] Appl. No.: 812,066

[22] Filed: Dec. 17, 1991

[51] Int. Cl.$^5$ .................... G01N 31/00; G01N 33/00
[52] U.S. Cl. ........................................ 436/14; 436/18; 436/66; 436/95; 436/176; 436/178; 436/811; 436/826
[58] Field of Search .............. 436/14, 18, 66, 95, 436/176, 178, 811, 826

[56] References Cited

U.S. PATENT DOCUMENTS

| | | | |
|---|---|---|---|
| 2,171,961 | 8/1938 | Fortune | 436/95 |
| 2,206,282 | 7/1940 | Jacobius | 436/95 |
| 2,863,733 | 12/1958 | Drey | 436/95 |
| 3,298,789 | 1/1967 | Mast | 436/95 |
| 3,350,278 | 10/1967 | Gretton et al. | 436/95 |
| 3,791,988 | 2/1974 | Josef et al. | 252/408 |
| 4,178,153 | 12/1979 | Sodickson | 23/230 R |
| 4,391,906 | 7/1983 | Bauer | 435/14 |
| 4,551,427 | 11/1985 | Draeger et al. | 435/14 |
| 4,780,419 | 10/1988 | Uchida et al. | 436/176 |
| 4,933,145 | 6/1990 | Uchida et al. | 422/61 |

OTHER PUBLICATIONS

John B. Hill and Phyllis Palmer, Filter Paper Blood Collection and Punching as a Means of Quantification, *Clinical Chemistry*, vol. 15, No. 5, 1969, pp. 381-389.

Nathan Gochman and Joan M. Schmitz, Application of a New Peroxide Indicator Reaction to the Specific, Automated Determination of Glucose with Glucose Oxidase, *Clinical Chemistry*, vol. 18, No. 9, 1972, pp. 943-950.

Richard B. Passey, Ronald L. Gillum, John B. Fuller, Francis M. Urry, and Mary Louise Giles, Evaluation and Comparison of 10 Glucose Methods and the Reference Method Recommended in the Proposed Product Class Standard (1974), *Clinical Chemistry*, vol. 23, No. 1, 1977, pp. 131-139.

Luis P. Leon, Douglas K. Chu, Lloyd R. Snyder and Csaba Horvath, Continuous-Flow Analysis for Glucose in Serum, with Use of Hexokinase and Glucose-6-Phosphate Dehydrogenase Co-Immobilized in Tubular Form, *Clinical Chemistry*, vol. 26, No. 1, 1980, pp. 123-129.

Timothy R. Gamlen, Howard C. James & Gifford F. Batstone, The Determination of Blood Spot Glucose Concentration Using a Rapid Kinetic Assay, *Scan. J. Clin. Lab. Invest*, 42, 1982, pp. 643-645.

Henning von Schenck, Linnea Lonnstrom, and Margareta Engstrom, Quality Control of Reflectometric Determinations of Glucose in Dried Blood Spots on Filter Paper, *Clinical Chemistry*, vol. 31, No. 5, 1985, pp. 706-709.

Jean Palardy, M.D., Jana Havrankova, M.D., Raymond Lepage, Ph.D., Ronald Matte, M.D., Raphael Belanger, M.D., Pierre D'Amour, M.D., and Louis-Georges St.--Marie, M.D., Blood Glucose Measurements During Symptomatic Episodes in Patients with Suspected Postprandial Hypoglycemia, *The New England Journal of Medicine*, vol. 321, No. 21, Nov. 23, 1989, pp. 1421-1425.

(List continued on next page.)

*Primary Examiner*—James C. Housel
*Assistant Examiner*—N. Bhat
*Attorney, Agent, or Firm*—D. A. N. Chase; Michael Yakimo, Jr.; Richard P. Stitt

[57] ABSTRACT

A method of stabilizing the glucose content of a blood sample applied to a sorbent for drying is provided. A solution of sodium fluoride or other glycolysis inhibitor is applied to a sorbent. A blood sample for glucose determination is then applied to the sorbent whereupon glycolysis is immediately inhibited. The blood sample may then be dried for shipping without loss of glucose content during the drying period.

22 Claims, No Drawings

OTHER PUBLICATIONS

K. Wakelin, D. J. Goldie, M. Hartog, and A. P. Robinson, Measurement of Capillary Blood Glucose in Filter-Paper Spots: an aid to the Assessment of Diabetic Control, *British Medical Journal*, 1978, 2, 468–469.

Kathleen Sazama, E. Arthur Robertson and Ruth A. Chesler, Is Antiglycolysis Required for Routine Glucose Analysis?, *Clinical Chemistry*, vol. 25, No. 12, 1979, pp. 2038–2039.

Wendell T. Caraway, Ph.D., and Nelson B. Watts, M.D., Carbohydrates, Chapter 6, Textbook of Clinical Chemistry, 1986 Edition, pp. 775–828.

METHOD OF GLUCOSE STABILIZATION AND ANALYSIS IN DRIED BLOOD SPOT SAMPLES

BACKGROUND OF THE INVENTION

Determination of glucose blood levels is one of the most frequently performed analyses in hospital laboratories. Glucose determinations are utilized for diagnosis and tracking of carbohydrate metabolism abnormalities such as hypoglycemia, diabetes mellitus as well as other conditions such as glucose levels in cerebrospinal fluid where meningitis is suspected.

Blood glucose levels fluctuate within a fairly narrow range. Variation in blood glucose is generally a result of changes in gross dietary circumstances such as feeding versus periods of fasting. However, detection of blood glucose levels which are above or below the normal range are indicative of some type of disease state. The most common disease associated with high blood glucose levels is diabetes mellitus. Serious diseases are rarely associated with low blood glucose levels and the common cause of low glucose blood levels is that the blood sample was taken during a fasting state in the subject.

In the insurance industry the health of the candidate is evaluated at the time of application for the insurance contract. It is common practice for an insurance company to send an on-site examiner to the individual seeking insurance and have a body fluid sample—blood—collected at a location most convenient for the individual. Heretofore, on-site examiners have collected blood by conventional methods such as venipuncture which results in large sample volumes. Recently an alternative method, by pricking the finger of the subject and dropping blood onto an sorbent layer, has become favored. The latter technique requires a much smaller blood volume and provides sample which ma be conveniently shipped to a central laboratory for testing.

"On-site" sample collection is by definition the collection of a sample under non-laboratory controlled conditions. One can either test the sample promptly on-site, which while possible is neither economical nor acceptable to insurance companies ordering such tests, or a valid test can be conducted by a properly qualified technician in a certified laboratory. Therefore, even though the sample maybe collected by a non-professional on-site, it must be conveyed to a central laboratory.

In many cases it is convenient, as well as necessary, to ship the sample to the laboratory by mail or courier in order to minimize the number of operations at the laboratory facility. In such case it is beneficial if the liquid sample can be reduced to a solid phase so as to avoid shipment of fluid blood samples. As a result it has recently been found advantageous to ship body fluid samples, blood in particular, as a dried spot on a sorbent matrix. In this manner the sample volume is reduced and the sample weight commensurately reduced by evaporation of the fluid component. The use of dried blood spot samples also avoids separation of plasma or serum from the cells by centrifugation. Thus is eliminated the inconvenience of either carrying about the centrifuge or taking samples to a central location for centrifugation within a short time after drawing the blood sample.

The technique for obtaining such a dried blood spot on a sorbent matrix involves pricking the finger of the subject and dropping the blood onto the sorbent layer at a specifically designated location and saturating that location with blood. The saturation of the sorbent matrix is followed by drying of the blood spot for sometime prior to insertion of the sorbent matrix into a mailing envelope for shipment to the laboratory.

For many components of blood the handling of the sample after application to the sorbent paper or matrix and the time of drying is not a critical factor for subsequent analysis. However, in the case of blood glucose determinations the handling of the blood sample by the on-site examiner is a critical aspect of the ultimate accuracy of glucose measurement in the sample. Once the blood sample is removed from the subject the physiological functioning of the cells within the blood sample continues. In the case of glucose, the entirety of the Embden-Meyerhof pathway continues to operate for sometime within the cells. This pathway is the principal method by which carbohydrates, and glucose in particular, are metabolized. Therefore, even though the blood sample is removed from the body the concentration of glucose within the blood sample will decrease over time unless glycolysis within the Embden-Meyerhof pathway is inhibited.

In blood samples in which glycolysis is not inhibited, the loss of glucose from the sample is generally estimated at 10 mg/deciliter(dl)/hour. Thus it is necessary to provide some type of means to inhibit glycolysis within the Embden-Meyerhof pathway in situations where immediate analysis of the glucose levels within a blood sample is not possible. When it is appreciated that the normal concentration of glucose in the blood of an adult is approximately 70–105 mg/dl of serum, it is apparent that the passage of even short periods of time can cause substantial reduction in the glucose content of the sample. Clearly such a high rate of glucose loss in a blood sample can rapidly cause incorrect measurement of glucose concentration in a subject's blood when applied to a untreated sorbent matrix.

Such a decrease in glucose concentration will be found when a blood sample is applied to a sorbent layer for shipment to a laboratory for subsequent glucose concentration analysis. One method of inhibiting the continuation of glycolysis in a blood sample applied to a sorbent layer is drying of the blood sample. The drying of the blood sample on the sorbent causes cessation of cellular activity by dehydration and subsequent termination of glycolysis within the cell. For the analysis of the glucose concentration in a blood sample to be accurate it is necessary that the drying of the sample on the sorbent layer be conducted immediately and that the blood sample be thoroughly dried prior to shipment of the sample to the laboratory.

However, in the course of sample collection by on-site examiners it is a frequent occurrence that the drying of the sample is delayed or that drying of the sample is never completely accomplished. This variation in the drying of the sample leads to variation in the decrease of glucose in samples taken from various subjects as well as in samples taken from the same subject.

In normal on-site sampling the on-site examiner is to obtain the blood sample by lancing a finger of the subject and squeezing drops of blood onto a sorbent layer. The application of the blood to the absorbent layer is to be immediately followed by drying the samples rapidly as possible. This is often accomplished by use of a heat gun to speed the drying process, but heating can also lead to baking the blood onto the sorbent matrix from which it may not then be eluted and therefore be unsuitable for analysis. When drying is accomplished quickly and rapidly minimum glucose loss due to cellular glycolysis is observed.

Since on-site examiners are not professional medical technicians, it is not uncommon for deviations from the approved protocol to occur. The drying of samples may not be done at all or very poorly or for variable time intervals or various portions of a single sample will be subjected to different rates of drying. This will result in disparate results within the same subject as well as between similar subjects. Also, it is not uncommon for samples to be placed in a shipping package without having been dried at all. Once blood is absorbed into the sorbent matrix, the examiner may assume that proper application is done and it is time to ship the sample. In such a case cellular functioning may continue for sometime and substantially deplete the glucose concentration in the sample rendering the sample unreliable for glucose determination.

Therefore, it is an object of the present invention to provide a method of glucose determination in a blood sample which will avoid the difficulties presented by the prior art methods.

Another object of the present invention is to provide a method of glucose determination which is independent of sample handling.

Yet another object of the present invention is to provide a method of glucose determination from a dried blood spot which avoids the variations in glucose concentration caused by improper and variable drying of the sample.

Yet another object of the present invention is to provide a method of field or on-site blood collection for subsequent glucose determination which rapidly and conveniently stabilizes the glucose content of the blood sample.

Another object of the present invention is to provide a method of field or on-site blood sampling for subsequent glucose determination which rapidly inhibits glycolysis in the blood sample.

Yet another object of the present invention is to provide a method of stabilizing a blood sample for subsequent glucose determination through collection of the blood sample on a conveniently and easily shipped substrate.

Yet another object of the present invention is to provide a method of obtaining a blood sample for subsequent glucose determination which involves drying the blood sample while maintaining a glucose concentration near that of a freshly obtained blood sample.

Yet another object of the present invention is to provide a method for inhibiting glucose degradation in a field blood sample which can be utilized at low cost.

Yet another object of the present invention is to provide a method which assists in avoiding the need to take repeat samples from subjects due to improper sampling procedures.

Other objects and advantages of this invention will become apparent from the following detailed description wherein is set forth by way of illustration and example, an embodiment of this invention.

SUMMARY OF THE INVENTION

In broad summary the method of the present invention takes advantage of the utility of certain chemical compounds to inhibit glycolysis in a blood sample obtained from a mammal. As a blood sample, though removed from a mammalian body, will continue for sometime to carry on biological functions at the cellular level, the concentration of glucose in the blood sample will diminish over time. The combination of an inhibiting substance with a sorbent material to which a blood sample is then applied serves to rapidly and conveniently inhibit glycolysis. While drying of the blood sample will eventually inhibit glycolysis, the method of the present invention avoids the variations in glucose concentrations due to variations in the length of drying time of the blood sample.

Inhibition of glycolysis on a sorbent matrix is accomplished by combining the sorbent with a glycolysis inhibitor such as sodium fluoride which causes a cessation of the conversion of glucose-1-phosphate into glucose-6-phosphate. Alternatively, inhibitors such as organic phosphates, citrate, halogen acetates, sodium iodoacetate, adenosine diphosphate, adenosine triphosphate or other earth metal fluorides such as potassium fluoride or lithium fluoride may be utilized to cause cessation of the conversion of glucose-1-phosphate to glucose-6-phosphate by inhibiting the Embden-Meyerhof pathway.

Once the blood sample has been dried on the inhibitor-containing matrix, the glucose is then removed from the dried sample while maintaining the blood proteins in a precipitated or solid state by combining the dried blood sample with an acid such as 5-sulfosalicylic acid or trichloroacetic acid, phosphotungstic acid, perchloric acid or benzoic acid.

After the glucose has been solubilized by the acid, the acid solution or supernate is then analyzed by conventional methods for glucose concentration. Three such methods are the glucose oxidase method, hexokinase method and o-toluidine method.

DETAILED DESCRIPTION

The invention is intended to operate in combination with what is known as dried blood spot (DBS) methodology of blood sample collection and transport. The DBS technology in its most general form consists of utilizing a sorbent layer or matrix to receive a blood sample from the subject then allowing the blood sample to dry on the sorbent. In general, utilizing the DBS methodology substantially reduces the sample volume of blood required to be transported and thereby avoids the dangers presented by shipment of the relatively large volumes of fluid blood required by other methodologies.

A sorbent layer or matrix or sorbent means may be such that the blood sample either adheres to the surfaces of the support means or matrix or alternatively is taken into the body of the support means. By way of example, not limitation the sorptive material may allow blood to be adsorbed onto its surfaces as with a sheet of glass, or alternatively, the blood may be absorbed into a cotton pad or absorbed into a volume of diatomaceous earth.

Once the sorptive layer or matrix has been selected it is treated with a glycolysis inhibiting compound. In the present invention the preferred glycolysis inhibitor is sodium fluoride which has been dissolved in a borate buffer system. To prepare the sorptive layer a solution of 18.72 grams of sodium fluoride (NaF) and 296.4 grams of boric acid are dissolved in six (6) liters of deionized water (0.312 percent w/v sodium fluoride and 4.94 percent w/v boric acid). This solution is then applied to the portions of the sorptive layer which will receive the blood sample at a concentration of approximately 0.23 ml to 0.5 ml per square inch. The sodium fluoride-borate buffer solution is allowed to dry on the absorbent layer.

Sodium iodoacetate may be substituted for sodium fluoride as the glycolysis inhibitor in the above solution. A solution of 12 grams of sodium iodoacetate and 296.4 grams of boric acid are dissolved in 6 liters deionized water (0.2 percent w/v sodium iodoacetate and 4.94 percent w/v boric acid). This solution is then used to coat the areas of the sorbent to which the blood sample will be applied. The sodium iodoacetate-boric acid solution is applied at a concentration of 0.23 ml to 0.5 ml per square inch.

There is no need within the methodology to allow the sodium fluoride-borate buffer solution to dry on the sorbent layer other than for convenience in handling and shipping of the sorbent layers to the examination site. The coated dried sorbent is then stored until used for sampling. It is preferred that the sorbent coated with the glycolysis inhibitor be stored at room temperature—approximately 25° centigrade—and in the presence of a desiccant. The sorbent layer or matrix so stored is stable for several months.

The utility and effectiveness of the inventive method of preventing a decrease in glucose concentration in blood is shown graphically in Table 1. A blood sample was applied to an

TABLE 1

Glucose concentration in dried blood spots over a four day period.

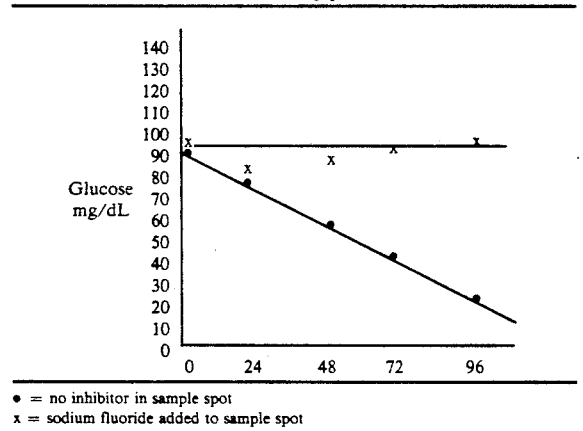

● = no inhibitor in sample spot
x = sodium fluoride added to sample spot untreated portion of a sorbent matrix. The same blood sample also was applied to a portion treated with sodium fluoride and allowed to dry. Both sample portions were tested for glucose concentration at T=0 hours; 24 hours; 48 hours; 72 hours; and 96 hours. The average decrease in five samples for each of the time periods was determined to be:

| T = 0 hours | 92.6 mg/dl |
| T = 24 hours | 76.8 mg/dl |
| T = 48 hours | 59.2 mg/dl |
| T = 72 hours | 45.4 mg/dl |
| T = 96 hours | 24 mg/dl |

However, in the blood samples applied to the sorbent utilizing the inventive method, the glucose concentration for each of the time periods was determined to be:

| T = 0 hours | 96 mg/dl |
| T = 24 hours | 86.2 mg/dl |
| T = 48 hours | 90 mg/dl |
| T = 72 hours | 91.6 mg/dl |
| T = 96 hours | 90.6 mg/dl |

When it is desired to test an individual for glucose blood concentration a finger of the subject is pricked with a lance o other suitable instrument and several droplets of blood are squeezed from the subject's finger onto the sorbent layer. As the blood contacts the sorbent layer it mixes with the sodium fluoride on the sorbent and the sodium fluoride then inhibits glycolysis within the blood sample. The sample is then transferred to the laboratory for analysis of the glucose content in the blood sample.

To simplify quantification of the blood sample applied to the sorbent, it is preferred to utilize a paper sorbent which is carefully controlled in its manufacture so as to provide consistent sorption of a particular volume of blood per area of paper. Examples of such a paper sorbent include an absorbent paper, S&S ® 903 ™, manufactured by Schleicher & Schuell, Inc. or equivalent papers from other vendors such as Whatman, Inc. of Clifton, N.J. Also, porous plastic having known sorption characteristics may be used in placed of cellulose or sponge absorbent materials.

As regards the absorbent, it is principally necessary that the material selected hold a known, reproducible quantity of blood when it is provided with sufficient sample to saturate the material. By use of such a material gravimetric determinations of the blood sample are eliminated. As the amount of blood sample required for adequate testing is known, it is only necessary to indicate on the sorbent layer the amount of area which should be saturated with the blood sample so as to provide sufficient sample quantity.

While it is preferred to use a absorbent which presents known absorptive characteristics, and therefore avoids the need for gravimetric or other determinations of the amount of sample on the absorbent, it is also possible to use any type of suitable absorbent followed by a gravimetric or other method of sample determination. Alternative acceptable sorbent matrices are cellulose fiber such as paper or cotton fiber or glass, fritted glass or diatomaceous earth, with a cellulose fiber such as paper being the preferred absorbent.

While sodium fluoride is the preferred inhibition agent it should be appreciated that alternative glycolysis inhibitors or inhibitors of the Embden-Meyerhof pathway generally can be substituted for sodium fluoride and achieve equivalent results in combination with a sorbent matrix upon which the blood sample is dried. Useful alternatives for sodium fluoride are other earth metal fluorides such as lithium fluoride or potassium fluoride. Examples of alternative inhibitors of the Embden-Meyerhof pathway are sodium iodoacetate, sodium oxalate, potassium oxalate, sodium citrate, potassium citrate and organic phosphates such as adenosine triphosphate and adenosine diphosphate.

After the on-site examiner has applied the blood sample to the sorbent layer and the blood has contacted the sodium fluoride or other glycolysis inhibitor, the blood sample is then dried for convenient shipment to the laboratory.

It should be noted that due to the inventive method of utilizing a glycolysis inhibitor with the sorbent material, the drying of the sample on the sorbent is no longer critical to successful and accurate determinations of glucose levels within the blood sample. As the sodium fluoride immediately inhibits glycolysis at the cellular level, the sample accuracy no longer depends upon the on-site examiner rapidly and efficiently drying the sample on the absorbent layer. Thus the inventive method which combines a means for inhibiting glycolysis with the sorbent layer or matrix serves to eliminate a major uncontrolled variable—drying of the sample—where the analysis of blood samples for glucose content is delayed for sometime.

At the analysis laboratory, two ⅛" circles are punched crisply from the center of the dried blood spot on the absorbent layer. It is necessary that the ⅛" circles be punched from the center of the sample area so as to avoid areas of incomplete saturation which may tend to exist towards the outer edges of the sample application area. In addition, it is necessary that the punched circles have smooth edges which do not have paper fibers clinging raggedly on the edges. These two aspects of circle punching procedure can contribute to anomalous sampling results and are to be avoided.

Once the ⅛" circles have been obtained they are placed into a small tube or into a micro well plate. A solution of an eluting buffer agent is the added to each well to dissolve the glucose from the sorbent material while keeping the blood protein components of the sample as a solid or a precipitate with the matrix. The punched circles should be thoroughly soaked with the buffer. Most punched circles absorb the eluting buffer and settle to the bottom of the container. Those which float may be pushed down into the buffer with a suitable means such as a steel needle or a thin applicator stick. The circles in the buffer solution are then mildly shaken for one hour at room temperature to ensure complete elution of the glucose into the buffer.

The composition of the eluting buffer agent in the preferred embodiment consists of a solution of 0.05 molar 5-sulfosalicylic acid in deionized water. The solution is made by first making a stock solution of 1 molar 5-sulfosalicylic acid by adding 218.2 grams of 5-sulfosalicylic acid to 1 liter of deionized water. This one molar (1.0M) stock solution is then diluted 1:20 with deionized water to result in a working eluting buffer solution of 0.05 molar 5-sulfosalicylic acid.

The eluting buffer agent used is also a protein precipitating agent which, while allowing the elution of glucose from the spotted circle, keeps the blood proteins precipitated to provide a clear supernatant free of interfering substances for analysis. The preferred acid for this precipitation is sulfosalicylic acid. However, other acids having a similar dissociation strength are equally suitable. Substitute acids such as trichloroacetic acid, phosphotungstic acid, perchloric acid or benzoic acid may be utilized with satisfactory results. In addition, alcohols such as ethanol may be used to precipitate the blood proteins, however, glucose does not dissolve as efficiently in these alcohols.

After the completion of the elution-precipitation step the sample is centrifuged to eliminate interference of floating particles and to pellet the blood proteins at the bottom of the sample. Centrifugation is conducted for 30 minutes at 3,000 rpm at room temperature after which the supernatant is transferred from the centrifugation container. The temperature, time, and rpm may vary depending on the centrifuge being used.

The glucose concentration of the supernatant is then analyzed using a conventional glucose assay such as the glucose oxidase methodology. In this method of glucose determination, glucose is oxidized to D-gluconate by glucose oxidase with the formation of an equimolar amount of hydrogen peroxide. The formed hydrogen peroxide is then utilized in the presence of the peroxidase enzyme to oxidize a chromogenic compound from its colorless form into its colored form. The absorbance of the colored compound is then determined in a spectrophotometer or colorimeter.

The reaction utilized with the inventive method utilizes 4-aminoantipyrine (4-AAP) and p-hydroxybenzene sulfonate (p-HBS) and hydrogen peroxide in the presence of peroxidase to form a quinoneimine dye. The absorbance of the resulting dye is then determined by measuring the absorbance in a spectrophotometer or colorimeter at 492 nanometers if standardly available commercial diagnostic kits for determination of glucose in serum may be utilized. The reaction scheme is:

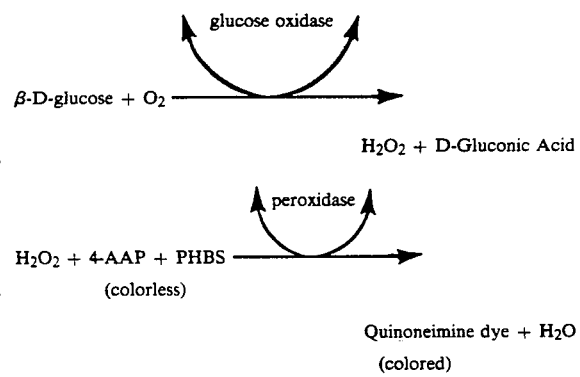

The reagent utilized to convert glucose to D-gluconic acid and to generate the quinoneimine dye is composed of phosphate buffer (500 mmol/l), 4-aminoantipyrine (3 mmol/l), p-hydroxybenzene sulfonate sodium salt ( 100 mmol/1), glucose oxidase (100,000 U/l, and peroxidase (horseradish) (50,000 U/l). Such a reagent is available from clinical chemistry supply companies.

For example one such in vitro diagnostic kit manufactured by Reagent Applications, Inc. of San Diego, Calif. calls for mixing the reagents for the development of the color compound in 500 ml of water. When utilized with the inventive methodology this volume is reduced to 100 ml to provide sufficient strength of the reagent to enable a sufficiently strong absorbance reading.

It should be appreciated that the color generating reagents of the peroxidase/hydrogen peroxide reaction can be replaced by a variety of compounds which are colorless in their reduced state but become colored in their oxidized state. This class of compounds known as leuco dyes, such as tetramethylbenzidine (TMB), o-phenylenediamine, guaiacol, benzidine, o-dianisidine, 2,2'-azino-di(3-ethylbenzthiazoline sulphonic acid-6) (ABTS), pyrogallol, 4-chloro-1-naphthol or nitrotetrazolium blue chloride may be oxidized to their colored state by peroxidase in the presence of peroxide.

Alternatively the determination of glucose may be achieved through use of standard preparations of the hexokinase method. This methodology consists of the following reaction scheme:

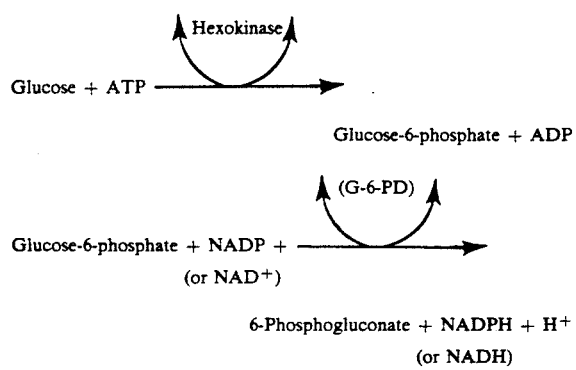

In the hexokinase methodology the hexokinase enzyme is utilized to catalyze a reaction between glucose and adenosine triphosphate (ATP) to form glucose-6-phosphate and adenosine diphosphate (ADP). The glucose-6-phosphate formed in the first reaction is, in the presence of glucose-6-phosphate dehydrogenase (G-6-PD), oxidized to 6-phosphogluconate with the reduction of $NAD^+$ to NADH. The increased concentration of NADH is directly proportional to the glucose concentration in the original sample. The NADH can be measured spectrophotometrically at 340 nanometers.

The glucose concentration of the unknown sample also may be determined utilizing a methodology based on the creation of a complex between o-toluidine and glucose. This methodology presents the following reaction scheme for creation of a colored compound the absorbance of which may be utilized to determine glucose concentration in the original sample.

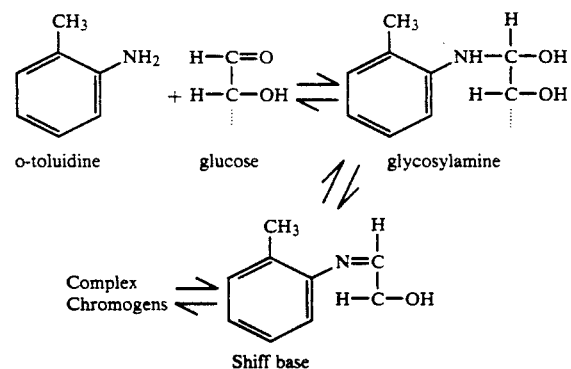

In the o-toluidine methodology a solution of thiourea (2.5 grams) and 500 ml of glacial acetic acid and 350 ml of saturated boric acid in deionized water are combined and mixed until the thiourea is dissolved. To this solution is added 150 ml of o-toluidine. This reagent is then added to 150 microliters of the supernatant from the dried blood spot sample and placed in a water bath at 100° centigrade for 10 minutes. The solution is then cooled for 2 to 3 minutes and remixed. The absorbance of the solution is read within 30 minutes at 630 nanometers. The absorbance obtained is then read against a graph of standard glucose concentrations and their absorbance (e.g. Table 2) for a determination of the glucose concentration of the unknown sample.

Once the absorbance of the glucose oxidase sample or hexokinase sample or o-toluidine sample has been determined, the glucose concentration in the sample is then read from a standard graph such as is shown in Table 2. The graph is constructed by performing the glucose-oxidase procedure or hexokinase procedure or o-toluidine procedure on known concentrations glucose standard (calibrator) circles and recording the absorbance or optical density readings as a function of the glucose concentrations. The calibrators are prepared in a normalized hematocrit free of all glucose using known accurate quantities of β-D-glucose. Each calibrator is treated as if it were a sample and is spotted on a sorbent matrix and dried. The glucose oxidase or hexokinase analysis procedure for glucose is then performed and the results determined colormetrically by observing absorbance. The

TABLE 2

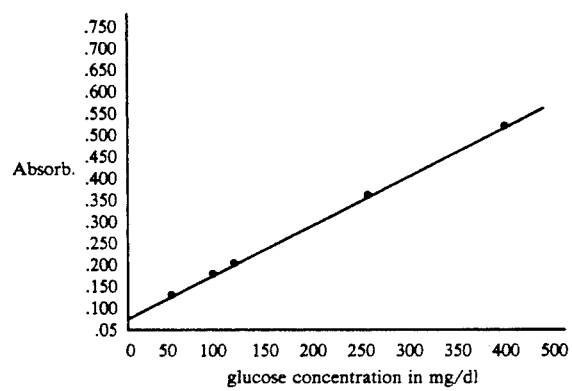

Standard curve of Glucose vs absorbence for determination of glucose concentration in blood samples absorbance results are then plotted against the known glucose concentration of the sample. This provides a standard curve of glucose concentration versus absorbance from which the absorbance of the actual blood samples may be read to provide the glucose concentration of the blood sample.

EXAMPLE 1

A blood sample is obtained from a subject by pricking the finger and dropping blood onto an absorbent paper which had been previously treated with a solution of sodium fluoride dissolved in boric acid and allowed to dry. After application of the blood sample to the paper, the blood was permitted to air dry. The card was then transported to the certified laboratory for elution of the glucose from the sample and testing for glucose concentration.

Elution and testing were accomplished by first punching duplicate ¼" circles from the center of the blood saturated paper and placing the circles into a well of a microtiter plate. To each well was added 250 microliters of a solution of 0.05 molar 5-sulfosalicylic acid. The plate was then gently rotated at 200 rps at room temperature for one hour to elute the glucose from the dried blood sample while keeping the blood proteins substantially in solid phase.

After shaking, the sample was centrifuged at 3000 rpm for 30 minutes to insure separation of the glucose containing sulfosalicylic acid supernatant from the paper and blood solids. A 150 microliter aliquot of the supernatant obtained from each blood sample was then transferred to separate wells of a clean flat-bottom microtiter plate. To each well was added 200 microliters of the glucose oxidase reagent and the plate covered and incubated for 15 minutes at 37° centigrade.

At the conclusion of the incubation period the absorbance of the solution of each well was determined at 492 nanometers. The absorbance was then compared to the standard graph (e.g. Table 2) for a determination of glucose concentration in the original blood sample.

EXAMPLE 2

A blood sample is obtained from a subject by any convenient method and the blood sample is dropped onto an absorbent paper until saturation of an area of approximately 0.2 square inches is obtained. The absorbent paper was previously treated with a solution of sodium iodoacetate (0.2 percent w/v sodium iodoacetate and boric acid 4.94 percent 2/v). After treatment with the sodium iodoacetate boric acid solution the sorbent was allowed to dry prior to application of the blood sample. After the blood sample was applied to the paper the blood was permitted to dry with the aid of warm air. The card was then sent to the laboratory for glucose determination.

In the laboratory duplicate ⅛ inch circles were punched from the center of the dried blood sample and the circles placed into wells of a microtiter plate. Each circle was then covered with 250 ml of a solution of trichloroacetic acid (0.05 molar) and the plate gently shaken at room temperature for about 1 hour to elute the glucose from the dried blood sample and into the trichloroacetic acid. The blood proteins were maintained in their precipitated state due to the trichloroacetic acid.

The samples were then centrifuged at 3000 rpm for 30 minutes to completely separate the solids from the glucose containing supernatant. A 150 microliter aliquot of the supernatant from each blood sample was then removed and placed into wells of a second microtiter plate. To each of the 150 microliter aliquots was added 200 microliters of the hexokinase reagent and the plate covered and incubated for 5 minutes at 37° centigrade. After the incubation period the absorbance was determined at 340 nanometers. The sample absorbance was then compared to a standard graph such as in Table 2 for determination of the glucose concentration in the original sample.

It is to be understood that while certain forms of this invention have been illustrated and described, it is not limited thereto, except insofar as such limitations are included in the following claims.

Having thus described the invention, what is claimed is new and desired to be secured by Letters Patent is as follows:

1. A method of preparing a blood sample and determining the glucose concentration thereof, said method comprising the steps of:
   contacting a sorbent with a solution of a means for inhibiting glycolysis;
   evaporating said solution to present a sorbent having said means for inhibiting glycolysis thereon;
   applying a fluid blood sample to said sorbent;
   drying said blood sample on said sorbent to present a dried blood sample;
   dissolving a glucose-containing portion of said dried blood sample in a solvent such that a blood protein portion of said dried blood sample substantially remains as a solid;
   separating said solvent from said solid;
   reacting said glucose-containing solvent with glucose oxidase enzyme and peroxidase enzyme in the presence of a peroxidase enzyme substrate molecule to produce an oxidized substrate molecule; and
   measuring the absorbance of said oxidized substrate molecule to proportionally determine the glucose concentration in the original blood spot.

2. The method as claimed in claim 1, wherein said means for inhibiting glycolysis is an earth metal fluoride.

3. The method as claimed in claim 1, wherein said means for inhibiting glycolysis is an organic phosphate.

4. The method as claimed in claim 1, wherein said means for inhibiting glycolysis is selected from the group consisting of sodium fluoride, potassium fluoride, potassium oxalate, sodium oxalate, citrate, adenosine diphosphate, adenosine triphosphate and sodium iodoacetate.

5. The method as claimed in claim 1, wherein said sorbent is selected from the group consisting of cellulose fiber, glass, fritted glass, cotton fiber, paper and diatomaceous earth.

6. The method as claimed in claim 1, wherein said solvent is an acid selected from the group consisting of sulfosalicylic acid, trichloroacetic acid, phosphotungstic acid, perchloric acid and benzoic acid.

7. The method as claimed in claim 1, wherein said solvent is an alcohol.

8. The method as claimed in claim 7, wherein said alcohol is selected from the group consisting of methyl alcohol, ethyl alcohol, and butyl alcohol.

9. A method of preparing a blood sample and determining the glucose concentration thereof, said method comprising the steps of:
   contacting a sorbent with a solution of a means for inhibiting glycolysis;
   evaporating said solution to present a sorbent having said means for inhibiting glycolysis thereon;
   applying a fluid blood sample to said sorbent;
   drying said blood sample on said sorbent to present a dried blood sample;
   dissolving a glucose portion of said dried blood sample in a solvent such that a blood protein portion of said dried blood sample substantially remains as a solid;
   separating the glucose-containing solvent from said solid;
   combining said glucose-containing solvent with o-toluidine and acetic acid to form a colored complex of glucose and o-toluidine; and
   determining the absorbance of said glucose and o-toluidine complex whereby to proportionally determine the glucose concentration in the original blood spot.

10. The method as claimed in claim 9, wherein said means for inhibiting glycolysis is an earth metal fluoride.

11. The method as claimed in claim 9, wherein said means for inhibiting glycolysis is an organic phosphate.

12. The method as claimed in claim 9, wherein said means for inhibiting glycolysis is selected from the group consisting of sodium fluoride, potassium fluoride, potassium oxalate, sodium oxalate, citrate, adenosine diphosphate, adenosine triphosphate and sodium iodoacetate.

13. The method as claimed in claim 9, wherein said sorbent is selected from the group consisting of cellulose fiber, glass, fritted glass, cotton fiber, paper and diatomaceous earth.

14. The method as claimed in claim 9, wherein said solvent is an acid selected from the group consisting of sulfosalicylic acid, trichloroacetic acid, phosphotungstic acid, perchloric acid and benzoic acid.

15. The method as claimed in claim 9, wherein said solvent is an alcohol.

16. The method as claimed in claim 15, wherein said alcohol is selected from the group consisting of methyl alcohol, ethyl alcohol, and butyl alcohol.

17. A method of preparing a blood sample and determining the glucose concentration thereof, said method comprising the steps of:

contacting a sorbent with a solution of a means for inhibiting glycolysis;
   evaporating said solution to present a sorbent having said means for inhibiting glycolysis thereon;
   applying a fluid blood sample to said sorbent;
   drying said blood sample on said sorbent to present a dried blood sample;
   dissolving a glucose-containing portion of said dried blood sample in a solvent such that a blood protein portion of said dried blood sample substantially remains as a solid;
   separating said solvent from said solid;
   converting the glucose in said solvent by introducing a glucose oxidase enzyme portion to produce a hydrogen peroxide portion;
   combining said hydrogen peroxide portion with a peroxidase enzyme substrate molecule;
   introducing a peroxidase enzyme portion to said hydrogen peroxide portion;
   oxidizing said substrate molecule with said peroxidase enzyme portion and said hydrogen peroxide portion to produce an oxidized substrate molecule; and
   measuring the absorbance of the oxidized substrate molecule whereby to proportionally determine the glucose concentration in the original blood spot.

18. The method as claimed in claim 17, wherein said means for inhibiting glycolysis is an earth metal fluoride.

19. The method as claimed in claim 17, wherein said means for inhibiting glycolysis is an organic phosphate.

20. The method as claimed in claim 17, wherein said means for inhibiting glycolysis is selected from the group consisting of sodium fluoride, potassium fluoride, potassium oxalate, sodium oxalate, citrate, adenosine diphosphate, adenosine triphosphate and sodium iodoacetate.

21. The method as claimed in claim 17, wherein said solvent is an acid selected from the group consisting of sulfosalicylic acid, trichloroacetic acid, phosphotungstic acid, perchloric acid and benzoic acid.

22. The method as claimed in claim 17, wherein said solvent is an alcohol.

* * * * *